United States Patent [19]

Persson

[11] Patent Number: 5,614,510
[45] Date of Patent: Mar. 25, 1997

[54] PHARMACEUTICAL COMPOSITION WITH IMPROVED BIOAVAILABILITY OF INOSITOL PHOSPHATE

[75] Inventor: Lars Persson, Hässleholm, Sweden

[73] Assignee: Perstorp AB, Sweden

[21] Appl. No.: 290,914

[22] PCT Filed: Feb. 23, 1993

[86] PCT No.: PCT/SE93/00144

§ 371 Date: Aug. 22, 1994

§ 102(e) Date: Aug. 22, 1994

[87] PCT Pub. No.: WO93/16705

PCT Pub. Date: Sep. 2, 1993

[30] Foreign Application Priority Data

Feb. 25, 1992 [SE] Sweden .................... 9200547

[51] Int. Cl.6 .................................. A61K 31/66
[52] U.S. Cl. ................ 514/103; 514/23; 514/104; 514/109; 514/554; 514/555; 514/556; 514/642; 514/643
[58] Field of Search ............... 536/26.74, 27.8; 514/23, 103, 104, 109, 554, 555, 556, 642, 643; 558/155

[56] References Cited

U.S. PATENT DOCUMENTS 4,851,560  7/1989  Siren ........................ 558/155
5,225,349  7/1993  Irth et al. ................... 436/105

FOREIGN PATENT DOCUMENTS

| 0342956 | 11/1989 | European Pat. Off. . |
| 0344997 | 12/1989 | European Pat. Off. . |
| 0349143 | 1/1990 | European Pat. Off. . |
| 7.873 | 4/1970 | France . |
| 3537569 | 5/1986 | Germany . |

OTHER PUBLICATIONS

Jonkman et al. (1983) "Ion Pair Absorption of Ionized Drugs—Fact or Fiction?" *Pharma. Weekblad Sci. Ed.*, 5: 41–48.

Chemical Abstracts, vol. 102, No. 1, 6465b, Jan. 7, 1985, p. 589 (Reg. No. 93712–95–9).

Primary Examiner—Shailendra Kumar
Attorney, Agent, or Firm—Scully, Scott, Murphy & Presser

[57] ABSTRACT

The invention relates to an inositol phosphate containing pharmaceutical composition which comprises a nitrogen-containing compound for improvement of the bioavailability of the inositol phosphate in mammals including man at non-parenteral administration. The invention also covers the use of at least one nitrogen-containing compound for the preparing of an inositol phosphate containing medicament with improved bioavailibility of inositol phosphate in mammals including man at non-parenteral administration.

16 Claims, No Drawings

PHARMACEUTICAL COMPOSITION WITH IMPROVED BIOAVAILABILITY OF INOSITOL PHOSPHATE

This application is a 371 of PCT/SE93/00144, filed Feb. 23, 1993.

The present invention relates to an inositol phosphate containing pharmaceutical composition with improved bioavailability of inositol phosphate and the use of at least one nitrogen-containing compound for the preparation of an inositol phosphate containing medicament with improved bioavailability of inositol phosphate.

Hydrophilic and ionized drugs must often encounter rather poor penetration of the epithelial barriers to the capillaries of the portal circulation as most of these types of substances are transported by passive diffusion. Inositol phosphates belong to this group.

Normally it is the unionized fraction of the drug that partitions across the lipid membranes and this fraction is most often small over the pH-range encountered in the gastrointestinal tract.

It is known from the literature, for example Jonkman J. H. G. and Hunt C. A. (1983) Pharmaceutische Weekblad Scientific Edition 5, 41–48, that a combination of a quarternary ammonium compound and sulfonic acids are absorbed to a small extent after oral administration. The absorption is described as poor and in many cases contradictory.

In the literature nothing has been described about the use of counter ions such as nitrogen-containing compounds together with inositol phosphates for improvement of the bioavailability.

At oral administration the properties of inositol phosphates per se result in limitations in respect of the uptake of the compounds from the intestine. In order to optimize the effect of these substances in the body it is desirable that as large a portion as possible of the added amount can be utilized effectively. Thereby the added amount can be reduced which is advantageous for the patient for example when the drug D-myo-inositol-1,2,6-trisphosphate ($IP_3$) is used.

According to the present invention it has now quite surprisingly been possible to meet the above desire and bring about an inositol phosphate containing pharmaceutical composition which comprises a nitrogen-containing compound for improvement of the bioavailability of the inositol phosphate in mammals including man at non-parenteral administration.

The expression bioavailability stands for a measurement of how large a portion of an administrated drug that occurs in the blood stream when the way of administration of the drug is non-parenteral. The term thus shows the amount of the drug that has been able to penetrate membrane barriers after for example oral administration, topical administration or intraperitoneal administration.

The nitrogen-containing compound can be for example a quarternary ammonium ion, a tertiary amine, a diamine, a polyamine, an amino acid or a derivative thereof.

The quarternary ammonium ions used according to the invention is defined as follows:

1. $^+N(R_1R_2R_3R_4)$ wherein $R_1$, $R_2$, $R_3$ and $R_4$ independently are (i) hydrogen (ii) a straight or branched alkyl with 1 to 24 carbon atoms such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, eicosyl and docosyl;

(iii) cycloalkyl with 3 to 16 carbon atoms such as cyclopropyl, cyclopentyl and cyclohexyl;

(iv) alkenyl with 2 to 24 carbon atoms such as vinyl, allyl, propenyl, octadienyl, octenyl, decenyl, dodecenyl, tetradecenyl, hexadecenyl, octadecenyl, octadecadienyl, nonadecenyl, octadecatrienyl and arachidonyl;

(v) cycloalkenyl with 5 to 16 carbon atoms such as cyclopentenyl, cyclopentadienyl, cyclohexenyl and cyclohexadienyl;

(vi) aryl with 6 to 24 carbon atoms such as phenyl and biphenyl;

(vii) aralkyl, alkaryl, aralkenyl, alkenylaryl wherein alkyl, aryl and alkenyl are as previously defined.

The above groups (ii) to (vii) are unsubstituted or substituted with hydroxy; oxo; alkoxy; aryloxy; carboxy; esterified carboxy; amino; substituted amino; formyl; acyl; acyloxy; or acylamine.

Preferred nitrogen-containing compounds in this group according to the invention are N-tetramethylammonium, N-tetraethylammonium, N-tetrapropylammonium, N-tetrabutylammonium, N-tetrapentylammonium, N-tetrahexylammonium, N-tetraheptylammonium and N-tetraoctylammonium. Other preferred nitrogen-containing compound are N-decyltrimethylammonium, N-undecyltrimethylammonium, N-dodecyltrimethylammonium, N-tridecyltrimethylammonium, N-tetradecyltrimethylammonoum, N-pentadecyltrimethylammonium, N-hexadecyltrimethylammonium, N-benzyltrimethylammonium.

2. $^+N(R_1R_2R_3)R_5$ wherein $R_1$, $R_2$, $R_3$ are as defined above and preferably methyl, ethyl or propyl and wherein $R_5$ is (i) $-(CH_2)_nOCOR_6$ wherein $n \geq 2$ and wherein $R_6$ is a straight or branched alkyl or alkenyl with 1 to 24 carbon atoms such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl eicosyl, docosyl, vinyl, allyl, octadienyl, octenyl, decenyl, dodecenyl, tetradecenyl, hexadecenyl, octadecenyl, octadecadienyl nonadecenyl, octadecatrienyl and/or arachidonyl or where $R_6$ is $-CH_2CH(CH_3)OCOR_1$, $-CH(CH_3)CH_2OCOR_1$, $-CH_2CH(OCOR_1)CH_2OCOR_1$, $-CH(CH_2OCOR_1)_2$, $-CH_2CH(OH)CH_2OCOR_1$, $-CH_2CH(CH_2OH)OCOR_1$, $-CH(CH_2OH)CH_2OCOR_1$ or $-CH(CH_3)COOR_1$ wherein $R_1$ is as defined above.

(ii) $-(CH_2)_nOR_6$ wherein n and $R_6$ are as defined above.

Preferred nitrogen-containing coumpounds in this group according to the invention are N-decanoyloxypropyltrimethylammonium, N-undecanoyloxypropyltrimethylammonium, N-dodecanoyloxypropyltrimethylammonium, N-tridecanoyloxypropyltrimethylammonium, N-tetradecanoyloxypropyltrimethylammonium, N-pentadecanoyloxypropyltrimethylammonium, N-hexadecanoyloxypropyltrimethylammonium, N-decanoyloxyethyltrimethylammonium, N-undecanoyloxyethyltrimethylammonium, N-dodecanoyloxy ethyltrimethylammonium, N-tridecanoyloxyethyltrimethylammonium, N-tetradecanoyloxyethyltrimethylammonium, N-pentadecanoyloxyethyltrimethyl-ammonium, N-hexadecanoyloxyethyltrimethylammonium, N-decyloxypropyltrimethylammonium, N-undecyloxypropyltrimethylammonium, N-dodecyloxypropyltrimethylammonium, N-tridecyloxypropyltrimethylammonium, N-tetradecyloxypropyltrimethylammonium, N-pentadecyloxypropyltrimethylammonium, N-hexadecyloxypropyltrimethylammonium, N-decyloxyethyltrimethylammonium, N-undecyloxyethyltrimethylammonium, N-dodecyloxyethyltrimethylammonium, N-tridecyloxyethyltrimethylammonium, N-tetradecyloxyethyltrimethylammonium, N-pentadecyloxyethyltrimethylammonium, N-hexadecyloxytrimethylammonium.

(iii) $-(C(R_7)_2)_n COOR_6$ wherein $n \geq 1$ and wherein $R_7$ is hydrogen and/or lower straight or branched alkyl such as methyl, ethyl, propyl, and/or butyl and wherein $R_6$ is as defined above. Preferably n=1 and $R_6$ is hexyl, heptyl, octyl, nonyl, decyl, dodecyl, tridecyl, tetradecyl, pentadecyl or hexadecyl.

(iv) $-C(R_7)_2 OCOR_6$ wherein $R_7$ is hydrogen and/or lower straight or branched alkyl such as methyl, ethyl, propyl and/or butyl and wherein $R_6$ is as defined above. Preferably $R_6$ is hexyl, hepty, octyl, nonyl, decyl, dodecyl, tridecyl, tetradecyl, pentadecyl or hexadecyl.

(v) $-C(R_7)_2)_n (C(R_8)_2)_m COOR_6$ wherein $n \geq 1$, $m \geq 1$ and wherein $R_7$ is as defined above, wherein $R_8$ is hydrogen, hydroxyl, alkyloxy or acyloxy and wherein $R_6$ is as defined above. Preferably the compounds are selected from the following group:

$^+N(CH_3)_3 CH_2 CHOHCH_2 COOR_6$ wherein $R_6$ is hexyl, heptyl, octyl, nonyl, decyl, dodecyl, tridecyl, tridecyl, tetradecyl, pentadecyl or hexadecyl;

$^+N(CH_3)_3 CH_2 CHOR_9 CH_2 COOR_6$ wherein $R_6$ is as defined above and wherein $R_9$ is lower alkyl such as methyl, ethyl and propyl or lower acyl such as formyl, acetyl or propionyl.

(vi) $-C(R_7)_2)_n CONR_7 CR_7 COOR_1$ wherein $n \geq 1$ and wherein $R_7$ is hydrogen and/or lower straight or branched alkyl such as methyl, ethyl, propyl and/or butyl and wherein $R_1$ is as defined above. Preferred n=1 and $R_7$ is hydrogen.

In one embodiment of this type of the invention $R_1$, $R_2$ and/or $R_3$ are i) hydrogen;

ii) a straight or branched alkyl selected from the group of methyl, ethyl, propyl, butyl, pentyl, hexyl, heptyl and/or octyl;

and $R_5$ is $-(CH_2)OCOR_6$ wherein $R_6$ is selected from the group of hexyl, heptyl, octyl, nonyl, decyl, dodecyl, tridecyl, tetradecyl, pentadecyl and/or hexadecyl.

In another embodiment of the invention $R_1$, $R_2$ and/or $R_3$ are i) hydrogen;

ii) a straight or branched alkyl selected from the group of methyl, ethyl, propyl, butyl, pentyl, hexyl, heptyl and/or octyl;

and $R_5$ is $(CH_2)OR_6$ wherein $R_6$ is selected from the group of hexyl, heptyl, octyl, nonyl, decyl, dodecyl, tridecyl, tetradecyl, pentadecyl and/or hexadecyl.

In another embodiment of the invention $R_1$, $R_2$ and/or $R_3$ are i) hydrogen;

ii) a straight or branched alkyl selected from the group of methyl, ethyl, propyl, butyl, pentyl, hexyl, heptyl and/or octyl;

and $R_5$ is $-C(R_7)_2 COOR_6$ wherein $R_6$ is selected from the group of hexyl, heptyl, octyl, nonyl, decyl, dodecyl, tridecyl, tetradecyl, pentadecyl and/or hexadecyl or from the group of $-CH_2CH(CH_3)OCOR_1$, $-CH(CH_3)CH_2OCOR_1$, $-CH_2CH(OCOR_1)CH_2OCOR_1$, $-CH(CH_2OCOR_1)_2$, $-CH_2CH(OH)CH_2OCOR_1$, $-CH_2CH(CH_2OH)OCOR_1$, $-CH(CH_2OH)CH_2OCOR_1$ or $-CH(CH_3)COOR_1$ and wherein $R_7$ is i) hydrogen;

ii) a straight or branched alkyl selected from the group of methyl, ethyl, propyl and/or butyl;

In still another preferred embodiment of the invention $R_1$, $R_2$ and/or $R_3$ are i) hydrogen;

ii) a straight or branched alkyl selected from the group of methyl, ethyl, propyl, butyl, pentyl, hexyl, heptyl and/or octyl;

and $R_5$ is $-C(R_7)_2 OCOR_6$ wherein $R_6$ is selected from the group of hexyl, heptyl, octyl, nonyl, decyl, dodecyl, tridecyl, tetradecyl, pentadecyl and/or hexadecyl and wherein $R_7$ is i) hydrogen;

ii) a straight or branched alkyl selected from the group of methyl, ethyl, propyl, butyl, pentyl, hexyl, heptyl and/or octyl;

3. A heterocyclic group containing at least one nitrogen atom such as $C_5H_4R_{10}NR_{11}$ wherein $R_{10}$ is hydrogen, lower alkyl, carboxy, esterified carboxy or carboxamide and wherein $R_{11}$ is (i) $R_1$ as defined above (ii) $-(C(R_7)_2)_n OCOR_6$ wherein $n \geq 1$ and wherein $R_7$ is hydrogen or lower alkyl such as methyl, ethyl, propyl and/or butyl and $R_6$ is as defined above.

Preferred nitrogen-containing compounds are 1-methyl-2-pyridine amide, 1-ethyl-2-pyridine amide, 1-propyl-2-pyridine amide, 1-methyl-3-pyridine amide, 1-ethyl-3-pyridine amide, 1-propyl-3-pyridine amide, 1-methyl-4-pyridine amide, 1-ethyl-4-pyridine amide, 1-propyl-4-pyridine amide.

Other preferred nitrogen-containing compounds are where n=1, $R_7$ is hydrogen and $R_6$ is hexyl, heptyl, octyl, nonyl, decyl, dodecyl, tridecyl, tetradecyl, pentadecyl.

The tertiary amines used according to the invention are:

(1) $N(R_1R_2R_3)$ wherein $R_1$, $R_2$ and $R_3$ independently are as defined above, Preferred nitrogen-containing compounds according to this type of the invention are octyldimethyl amine, nonyldimethyl amine, decyldimethyl amine, undecyldimethyl amine, dodecyldimethyl amine, tridecyldimethyl amine, tetradecyldimethyl amine, pentadecyldimethyl amine or hexadecyldimethyl amine.

(2) A heterocylic group containing at least one nitrogen atom such as $C_5H_5R_{10}N$ wherein $R_{10}$ is hydrogen, lower alkyl, carboxy, esterified carboxy or carboxamide. Preferred nitrogen-containing compounds are 2-pyridine amide, 3-pyridine amide and 4-pyridine amide.

Other amines are also to be contemplated to be in the scope of the invention. These include for example diamines and polyamines such as alkyllysine, alkylarginine, alkylhistidine and guanidin or derivatives thereof.

Preferred compounds according to this embodiment of the invention are ethyllysine, propyllysine, butyllysine, ethylarginine, propylarginine, butylarginine, ethylhistidine, propylhistidine and butylhistidine.

Other nitrogen-containing compounds within the scope of the invention are amino acids such as arginine, lysine, histidine, creatinine or their derivatives and polyamino acids such as polylysine and polyornithine.

Still other nitrogen-containing compounds related to the invention are cationic polymers such as aminopolysaccharides.

When the nitrogen-containing compound is a quarternary ammonium ion an ion-pair structure can be formed between the compound and inositol phosphate. This can also be the case for other nitrogen-containing compounds when they are protonated depending on the pH.

An ion-pair structure is a non-covalent interaction, for example, between one or more quarternary ammonium ions and one or more inositol phosphates, as described in the following formula:

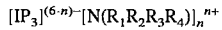

$$[IP_3]^{(6-n)-}[N(R_1R_2R_3R_4)]_n^{n+}$$

The expression inositol phosphate comprises different isomers of inositol for example myo-inositol, allo-inositol, cis-inositol, chiro-inositol, scyllo-inositol, muco-inositol, neo-inositol or epi-inositol. Most often the inositol isomer is myo-inositol.

The degree of phosphorylation can vary between one phosphate group/inositol moiety to six phosphate groups/inositol moiety.

Preferably inositol trisphosphate isomers are used according to the invention and most preferably D-myo-inositol-1,2,6-trisphosphate ($IP_3$) is used.

According to the invention the inositol phosphate is most often present in a salt form or in a form where only a few of the negative charges are protonated. The salt can contain one or more cations in different combinations. Examples of cations are sodium and potassium ions. When the ion-pair structure is formed with a nitrogen-containing compound such as a quarternary ammonium ion one or more of the protons and cations will be replaced with the quarternary ammonium ions.

The pharmaceutical composition according to the invention may be administered orally, topically, rectally or by inhalation spray in dosage forms or formulations comprising conventional, non-toxic pharmaceutically acceptable carriers, adjuvants and vehicles.

The pharmaceutical composition for oral use can be present in different forms such as capsules, granules, tablets, troches, lozenges, aqueous suspensions, dispensible powders, emulsions, syrups or elixirs. When the composition is present in liquid form capsules are preferably utilized. At the use of granules, these preferably have a size of 0.15–2 mm. Either the granules can consist of the pharmaceutical composition per se or of the composition and suitable fillers. When the pharmaceutical composition is used in a tablet form, the tablets can have a weight of 50–1500 m, for example preferably 50–800 mg and most preferably 100–500 mg.

Formulations for oral use include tablets which contain the active ingredient in a mixture with non-toxic pharmaceutically acceptable excipients. These excipients may be, for example, inert diluents, such as calcium carbonate, sodium chloride, lactose, calcium phosphate or sodium phosphate; granulating and disintegrating agents, for example, potato starch, or alginic acid; binding agents, for example, starch, gelatin or acacia; and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin, or olive oil.

For the rectal application of the composition of this invention, typical dosage forms include suppositories, rectal gelatin capsules (solutions and suspensions), and enemas or micro-enemas (solutions and suspension). Thus, in a typical suppository formulation, any one of the compounds of this invention is combined with any pharmaceutically acceptable suppository base such as cocoa butter, esterified fatty acids, glycerinated gelatin, and various water-soluble or dispersible bases like polyethylene glycols and polyoxyethylene sorbitan fatty acid ester. Various additives like salicylates or surfactant materials may be incorporated.

For topical use, creams, ointments, gels, solutions or the like containing the compositions are employed according to methods recognized in the art.

Naturally, therapeutic dosage ranges for the compounds of the present invention will vary with the size and needs of the patient and the particular pain or disease symptom being treated.

The administration of the pharmaceutical composition according to the invention can be in a combined dosage form or in separate dosage forms.

As mentioned above the invention also relates to the use of at least one nitrogen-containing compound for the preparation of an inositol phosphate containing medicament with improved bioavailability of inositol phosphate in mammals including man at non-parenteral administration.

The nitrogen-containing compound can be a quarternary ammonium compound, a tertiary amine, a diamine, a polyamine, an amino acid or a derivative thereof as defined above.

Preferably the inositol phosphate is inositol trisphosphate and most preferably the inositol trisphosphate is D-myo-inositol-1,2,6-triphosphate.

Another embodiment of the invention relates to pharmaceutical compositions comprising a nitrogen-containing compound and other phosphorus-containing inositol derivatives. For example different types of phosphonates of inositol encounter the need of improved bioavailability after non-parenteral administration. Still another embodiment of the invention relates to pharmaceutical compositions comprising a nitrogen-containing compound and derivatives of inositol phosphates and inositol phosphonates. The derivatives could be compounds where the phosphate or phosphonate group or groups are further esterified or compounds where the hydroxyl groups on the inositol moiety are etherified or esterfied, such as alkanoyl and carbamoyl derivatives. A further embodiment of the invention is related to compositions comprising a nitrogen-containing compound and inositol derivatized with other charged groups such as carboxyl and sulphonyl. The nitrogen-containing compounds used in these embodiments belong to the same groups as disclosed above.

The invention also relates to the improvement of the penetration of cell membranes in a wider aspect than in the above definition of bioavailability. Under certain circumstances there is a need to be able to obtain an improved ability of different isomers of inositol phosphates or derivatives thereof to cross cell membranes.

Such an example is when it is desirable to let the inositol phosphate or its derivative influence different intracellular metabolic pathways. This can be the case for example when new drugs based on inositol phosphate compounds are being developed. Another example is when the knowledge of different cellular signal systems is further explored. For example it is known that some isomeric structures of inositol phosphates exist intracellularly. In many cases it is advantageous to be able to add these substances from the extracellular space in order to clarify in more detail how they effect the behaviour of the cells. This knowledge can then be used in order to develop agonistic or antagonistic compounds effecting the cellular response.

The combination of a nitrogen-containing compound such as a quarternary ammonium ion and an inositol phosphate or its derivative will facilitate the penetration across cellular membranes.

Another area is when it is desirable to facilitate the transport of nucleoside across cellular membranes.

The combination of a nitrogen-containing compound such as a quarternary ammonium ion and a nucleoside will enhance the penetration of cellular membranes.

Furthermore the invention can be used for other pharmaceuticals which suffer from low bioavailability due to the same reasons as inositol phosphates and their derivatives. One such application is a pharmaceutical composition comprising a nitrogen-containing compound and a biophosphonate or a derivative thereof useful for the treatment of bone disorders such as osteoporosis and other conditions characterized by abnormal calcium metabolism.

The bisphosphonate or the derivative thereof could be selected from the group of hydroxy ethane bisphosphonate, amino ethane bisphosphonate, dichloromethylene bisphosphonate, methylene bisphosphonate, and preferably:

1-hydroxy-3-aminopropane-1,1-bisphosphonate
1-hydroxy-6-aminohexane-1,1-bisphosphonate
4-amino-1-hydroxybutylidene-1,1-bisphonate
N-methyl-4-amino-1-hydroxy-butylidene-1,1-bisphosphonate
3-amino-1-hydroxypropylidene-1,1-bisphosphonate
1-hydroxy ethylidene-1,1-bisphosphonate
4-(hydroxy methylene-bisphosphonate)piperidine.

Another application is a pharmaceutical composition comprising a nitrogen-containing compound and a bisphosphonate or a derivative thereof useful for the treatment of cardiovascular conditions such as increased cholesterol levels and atherosclerosis. The biophosphonate or the derivative thereof could be selected from the group of alkyl bisphosphonates, alkenyl bisphosphonates, alkynyl bisphosphonates, phenyl alkyl bisphosphonates and phenoxyalkyl bisphosphonates.

Still another application is a pharmaceutical composition comprising nitrogen-containing compound and a specific bisphosphonate useful as antimicrobial agents. The bisphosphonate in this application is selected from the group of alkyl ethenylidene bisphosphonates such as tetraisopropyl ethenylidene bisphosphonate and diethyl dibutyl ethenylidene bisphosphonate. The invention can also be used for other pharmaceuticals suffering from low bioavailability such as antiviral agents. One such application is a pharmaceutical composition comprising a nitrogen-containing compound and a charged phosphorus-containing pharmaceutical or a biologically active compound such as:

phosphonoformiate
phosphonoacetate
3-azido thymidine-5-phosphate
9-(2-phosphonyl methoxy ethyl)adenine
S-9-(3-hydroxy-2-phosphonyl methoxy propyl)-adenine/cytosine
2',3'-didehydro-2,3-dideoxy thymidine
(2R,5R)-9-(2,5-dihydro-5-phosphonomethoxy)-2-furanyl adenosine and derivative thereof. The compositions are useful for the treatment of CMV-infections. HIV-infections, herpes simplex and hepatitis B.

The invention can also be used for other pharmaceuticals and biologically active compounds with low and limited bioavailability such as phosphorylated and phosphonylated sugar residues, for example hydroxy phosphonyl glucoseamine derivatives, purine and pyrimidine nucleotides and derivatives thereof for example 2'-deoxy-5-fluorouridine 5'-phosphate and oligonucleotides and derivatives thereof. Those skilled in the art will realize that the list of compounds is not exhaustive and the invention is also applicable to other pharmaceuticals and biologically active compounds comprising a phosphate or phosphonate moiety.

The invention will be explained further in connection with the embodiment examples below, however without limiting it thereto.

Example 1 shows the manufacturing of pharmaceutical composition comprising a quarternary ammonium ion and $IP_3$. Example 2 and 3 illustrates the determination of the bioavailability of two different quarternary ammonium ions and $IP_3$ after oral administration while example 4 describes the bioavailability of a composition comprising a tertiary amine and $IP_3$.

EXAMPLE 1

The pentasodium salt of D-myo-inositol-1.2.6-triphosphate ($IP_3$), 2.0 g, was converted to the acid form by a cation exchanger in acid form. To a concentrated solution of the acid form of $IP_3$ was added 3.7 g of N(3-dodecanoyl oxy)propyltrimethylammonium hydroxide to form an ion-pair structure consisting of 3 moles of the quarternary ammonium ion/$IP_3$-moiety.

EXAMPLE 2

The bioavailability of N(3-dodecanoyloxy)propyltrimethylammonium inositol trisphosphate (obtained according to Example 1) after oral administration was determined in an experiment with pigs. Five pigs were given an intravenous injection of the sodium salt of D-myo-inositol-1.2.6-trisphosphate ($IP_3$) and blood samples were collected 0.25 hr, 0.5 hr, 1 hr, 4 hrs, 6 hrs, 8 hrs and 24 hrs after the injection. The blood samples were assayed for the content of $IP_3$ and these measurements were used for the calculation of the reference data as 100% of the substance is introduced into the blood stream after an intravenous injection.

Another five pigs were given the N(3-dodecanoyloxy)propyltrimethyl ammonium salt of $IP_3$ as an intraduodenal dosing. The animals were treated with Atropin® and anaesthetized with Hypnodil®/Sedaperone® whereafter a laparotomy was carried out. Blood samples were collected at the time intervals mentioned above and the concentration of $IP_3$ was determined in each sample. By calculating the area under the curve (AUC) from a graph where the concentration versus time is shown and comparing the obtained value with a similar calculation from the data after intravenous injection of the substance the bioavailability for the specific formulation is obtained.

Still another five pigs were given the penta-sodium salt of $IP_3$ orally. Blood samples were collected at the same time intervals as above and the concentration of $IP_3$ was determined. Following a similar procedure the AUC was determined.

The following concentrations of $IP_3$ were obtained after intravenous injection of the sodium salt, after oral administration of the N(3-dodecanoyl-oxy)propyltrimethyl ammonium salt and after oral administration of the sodium salt respectively.

| time (hrs) | intravenous injection, sodium salt | conc. $IP_3$ (μM) oral formulation, quarternary ammonium salt | oral formulation, sodium salt |
|---|---|---|---|
| 0 | 0 | 0 | 0 |
| 0.25 | 71.0 | 6.3 | 0.2 |
| 0.5 | 47.5 | 9.4 | 0.5 |
| 1.0 | 24.9 | 10.8 | 0.5 |
| 2.0 | 9.3 | 7.6 | 0.2 |
| 4.0 | 3.2 | 2.2 | 0.1 |
| 6.0 | 1.1 | 1.0 | 0.1 |
| 8.0 | 0.4 | 0.8 | 0 |
| 24.0 | 0.2 | 0.1 | 0 |
| Normalized AUC (%) | 100 | 46 | 3 |

The bioavailability of the oral formulation consisting of the quarternary ammonium salt of $IP_3$ was 46%.

EXAMPLE 3

The bioavailability of N-(hexyloxycarbonyl)methyl trimethyl ammonium inositol trisphosphate after oral administration was determined with a method similar to the description in Example 2. Five pigs were given an intravenous injection of the penta-sodium salt of $IP_3$ while another five animals were given a formulation consisting of the quarternary ammonium salt of $IP_3$ as an intraduodenal dosing. Still another group of five pigs were given the penta-sodium salt of $IP_3$ orally. Blood samples were collected and the concentration of $IP_3$ were determined.

The following concentrations of $IP_3$ were obtained after intravenous injection of the sodium salt after oral administration of the N-(hexyloxycarbonyl)methyltrimethyl ammonium salt and after oral administration of the sodium salt respectively.

| time (hrs) | intravenous injection, | conc. $IP_3$ (μM) oral formulation, quarternary ammonium salt | oral formulation, sodium salt |
|---|---|---|---|
| 0 | 0 | 0 | 0 |
| 0.25 | 71.0 | 18.2 | 0.2 |
| 0.5 | 47.5 | 29.6 | 0.5 |
| 1.0 | 24.9 | 20.1 | 0.5 |
| 2.0 | 9.3 | 12.2 | 0.2 |
| 4.0 | 3.2 | 4.3 | 0.1 |
| 6.0 | 1.1 | 1.5 | 0.1 |
| 8.0 | 0.4 | 0.6 | 0 |
| 24.0 | 0.2 | 0.1 | 0 |
| Normalized AUC (%) | 100 | 75 | 3 |

The bioavailability of the oral formulation consisting of the quarternary ammonium salt of $IP_3$ was 75%. Irritancy test showed no toxic effects on the intestinal barriers.

EXAMPLE 4

The bioavailability of a formulation consisting of dodecyldimethyl amine and D-myo-inositol-1.2.6-trisphosphate ($IP_3$) after oral administration was determined with a method similar to the description in Example 2. Five pigs were given an intravenous injection of the penta-sodium salt of $IP_3$ while another five animals were given a formulation consisting of dodecyldimethyl amine and $IP_3$ as an intraduodenal dosing. Still another group of five pigs were given the penta-sodium salt of $IP_3$ orally. Blood samples were collected and the concentration of $IP_3$ were determined.

The following concentrations of $IP_3$ were obtained after intravenous injection of the sodium salt, after oral administration of the formulation consisting of dodecyldimethyl amine and $IP_3$ and after oral administration of the sodium salt of $IP_3$ respectively.

| time (hrs) | intravenous injection, | oral formulation, tertiary amine composition | conc. $IP_3$ (μM) oral formulation, sodium salt |
|---|---|---|---|
| 0 | 0 | 0 | 0 |
| 0.25 | 71.0 | 2.8 | 0.2 |
| 0.5 | 47.5 | 4.2 | 0.5 |
| 1.0 | 24.9 | 4.0 | 0.5 |
| 2.0 | 9.3 | 3.8 | 0.2 |
| 4.0 | 3.2 | 1.7 | 0.1 |
| 6.0 | 1.1 | 0.8 | 0.1 |
| 8.0 | 0.4 | 0.6 | 0 |
| 24.0 | 0.2 | 0.1 | 0 |
| Normalized AUC (%) | 100 | 23 | 3 |

The bioavailability of the oral formulation consisting of the amine composition was 23%.

I claim:

1. An inositol phosphate containing pharmaceutical composition comprising an ion-pair structure obtained by combining an inositol phosphate with a compound of the formula $^+N(R_1R_2R_3)R_5$ wherein $R_1$, $R_2$ and $R_3$ are independently
   i) hydrogen
   ii) a straight or branched alkyl with 1 to 24 carbon atoms,
   iii) cycloalkyl with 3 to 16 carbon atoms,
   iv) alkenyl, with 2 to 24 carbon atoms,
   v) cycloalkenyl with 5 to 16 carbon atoms,
   vi) aryl with 6 to 24 carbon atoms or
   vii) aralkyl, alkaryl, aralkenyl, alkenaryl wherein alkyl, aryl and alkenyl are as previously defined,
the above groups (ii) to (vii) being unsubstituted or substituted with hydroxy, oxo, alkoxy, aryloxy, carboxy, esterified carboxy, amino, substituted amino, formyl, acyl, aryloxy or acylamine and $R_5$ is
   i) —$(CH_2)_n OCOR_6$ wherein $n \geq 2$ and wherein $R_6$ is
      (1) a straight or branched alkyl with 1 to 24 carbon atoms,
      (2) alkenyl with 2 to 24 carbon atoms or
      (3) —$CH_2CH(CH_3)OCOR_1$, —$CH(CH_3)CH_2OCOR_1$, —$CH_2CH(OCOR_1)CH_2OCOR_1$, —$CH(CH_2OCOR_1)_2$, —$CH_2CH(OH)CH_2OCOR_1$, —$CH_2CH(CH_2OH)OCOR_1$, —$CH(CH_2OH)CH_2OCOR_1$ or —$CH(CH_3)COOR_1$ wherein $R_1$ is as defined above,
   ii) —$(CH_2)_n OR_6$ wherein n and $R_6$ are as defined above
   iii) —$(C(R_7)_2)_n COOR_6$ wherein $n \geq 1$ and wherein $R_6$ is as defined above and wherein $R_7$ is
      (1) hydrogen, or
      (2) methyl, ethyl, propyl, butyl or pentyl
   iv) —$C(R_7)_2 OCOR_6$ wherein $R_6$ and $R_7$ are as defined above,
   for improvement of the bioavailability of the inositol phosphate in a mammal at non-parenteral administration.

2. A composition according to claim 1 wherein $R_1$, $R_2$ and/or $R_3$ are i) hydrogen or ii) a straight or branched alkyl selected from the group of methyl, ethyl, propyl, butyl, pentyl, hexyl and/or octyl; and wherein $R_5$ is —$(CH_2)OCOR_6$ wherein $R_6$ is selected from hexyl, heptyl, octyl, nonyl, decyl, dodecyl, tridecyl, tetradecyl, pentadecyl and/or hexadecyl.

3. A composition according to claim 1 wherein $R_1$, $R_2$ and/or $R_3$ are i) hydrogen or ii) a straight or branched alkyl selected from the group of methyl, ethyl, propyl, butyl, pentyl, hexyl, hepty and/or octyl; and wherein $R_5$ is —$(CH_2)_2OR_6$ wherein $R_6$ is selected from the group of hexyl, heptyl, octyl, nonyl, decyl, dodecyl, tridecyl, tetradecyl, pentadecyl and/or hexadecyl.

4. A composition according to claim 1 wherein $R_1$, $R_2$ and/or $R_3$ are i) hydrogen or ii) a straight or branched alkyl selected from the group of methyl, ethyl, propyl, butyl, pentyl, hexyl, heptyl and/or octyl; and wherein $R_5$ is —$C(R_7)_2COOR_6$ wherein $R_6$ is selected from the group of hexyl, heptyl, octyl, nonyl, decyl, dodecyl, tridecyl, tetradecyl, pentadecyl and/or hexadecyl and wherein $R_7$ is i) hydrogen or ii) a straight or branched alkyl selected from the group of methyl, ethyl, propyl and/or butyl.

5. A composition according to claim 1 wherein $R_1$, $R_2$ and/or $R_3$ are i) hydrogen or ii) a straight or branched alkyl selected from the group of methyl, ethyl, propyl, butyl, pentyl, hexyl, heptyl and/or octyl; and wherein $R_5$ is —$C(R_7)_2COOR_6$ wherein $R_6$ is selected from the group of hexyl, heptyl, octyl, nonyl, decyl, dodecyl, tridecyl, tetradecyl, pentadecyl and/or hexadecyl and wherein $R_7$ is i) hydrogen or ii) a straight or branched alkyl selected from the group of methyl, ethyl, propyl and/or butyl.

6. A composition according to any one of claims 1–5, wherein the inositol phosphate is at least one specific isomer of inositoltriphosphate ($IP_3$).

7. A composition according to claim 6, wherein the isomer of $IP_3$ is D-myo-inositol-1,2,6-triphosphate.

8. A composition according to any one of claims 1–7 in capsule, tablet or granulated form.

9. A composition according to any one of claims 1–7 in a combined dosage form.

10. A method for improving bioavailability in a mammal of an inositol phosphate, comprising administering to said mammal an ion-pair structure obtained by combining an inositol phosphate with a compound of the formula $^+N(R_1R_2R_3)R_5$ wherein $R_1$, $R_2$ and $R_3$ are independently i) hydrogen ii) a straight or branched alkyl with 1 to 24 carbon atoms, iii) cycloalkyl with 3 to 16 carbon atoms, iv) alkenyl, with 2 to 24 carbon atoms v) cycloalkenyl with 5 to 16 carbon atoms, vi) aryl with 6 to 24 carbon atoms or vii) aralkyl, alkaryl, aralkenyl, alkenaryl wherein alkyl, aryl and alkenyl are as previously defined, the above groups (ii) to (vii) being unsubstituted or substituted with hydroxy, oxo, alkoxy, aryloxy, carboxy, esterified carboxy, amino, substituted amino, formyl, acyl, aryloxy or acylamine and $R_5$ is i) —$(CH_2)_nOCOR_6$ wherein $n \geq 2$ and wherein $R_6$ is (1) a straight or branched alkyl with 1 to 24 carbon atoms, (2) alkenyl with 2 to 24 carbon atoms or (3) —$CH_2CH(CH_3)OCOR_1$, —$CH(CH_3)CH_2OCOR_1$, —$CH_2CH(OCOR_1)CH_2OCOR_1$, —$CH(CH_2OCOR_1)_2$, —$CH_2CH(OH)CH_2OCOR_1$, —$CH_2CH(CH_2OH)OCOR_1$, —$CH(CH_2OH)CH_2OCOR_1$ or —$CH(CH_3)COOR_1$ wherein $R_1$ is as defined above, ii) —$(CH_2)_nOR_6$ wherein n and $R_6$ are as defined above, iii) —$(C(R_7)_2)_nCOOR_6$ wherein $n \geq 1$ and wherein $R_6$ is as defined above and wherein $R_7$ is (1) hydrogen or (2) methyl, ethyl, propyl, butyl or pentyl or iv) —$C(R_7)_2OCOR_6$ wherein $R_6$ and $R_7$ are as defined above.

11. The method according to claim 10, wherein the inositol phosphate is an isomer of inositoltriphosphate.

12. The method according to claim 11, wherein the isomer of inositoltriphosphate is D-myo-inositol-1,2,6-tris-phosphate.

13. The inositol phosphate according to claim 1 wherein $R_1$, $R_2$ and $R_3$ are independently hydrogen, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, eicosyl, docosyl, cyclopropyl, cyclopentyl, cyclohexyl, vinyl, allyl, propenyl, octadienyl, octenyl, decenyl, dodecenyl, tetradecenyl, hexadecenyl, octadecenyl, octadecadienyl, nonadecenyl, octadecatrienyl, arachidonyl, cyclopentenyl, cyclopentadienyl, cyclohexenyl, cyclohexadienyl, phenyl, biphenyl, aralkyl, alkaryl, aralkenyl or alkenaryl, said $R_1$, $R_2$ and $R_3$ being unsubstituted or substituted with hydroxy, oxo, alkoxy, aryloxy, carboxy, esterified carboxy, amino, substituted amino, formyl, acyl, aryloxy or acylamine.

14. The inositol phosphate according to claim 1 wherein $R_6$ is methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, eicosyl, docosyl, vinyl, allyl, propenyl, octadienyl, octenyl, decenyl, dodecenyl, tetradecenyl, hexadecenyl, octadecenyl, octadecadienyl, nonadecenyl, octadecatrienyl, arachidonyl, —$CH_2CH(CH_3)OCOR_1$, —$CH(CH_3)CH_2OCOR_1$, —$CH_2CH(OCOR_1)CH_2OCOR_1$, —$CH(CH_2OCOR_1)_2$, —$CH_2CH(OH)CH_2OCOR_1$, —$CH_2CH(CH_2OH)OCOR_1$, —$CH(CH_2OH)CH_2OCOR_1$ or —$CH(CH_3)COOR_1$.

15. The method according to claim 10 wherein $R_1$, $R_2$ and $R_3$ are independently hydrogen, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, eicosyl, docosyl, cyclopropyl, cyclopentyl, cyclohexyl, vinyl, allyl, propenyl, octadienyl, octenyl, decenyl, dodecenyl, tetradecenyl, hexadecenyl, octadecenyl, octadecadienyl, nonadecenyl, octadecatrienyl, arachidonyl, cyclopentenyl, cyclopentadienyl, cyclohexenyl, cyclohexadienyl, phenyl, biphenyl, aralkyl, alkaryl, aralkenyl or alkenaryl, said $R_1$, $R_2$ and $R_3$ being unsubstituted or substituted with hydroxy, oxo, alkoxy, aryloxy, carboxy, esterified carboxy amino, substituted amino, formyl, acyl, aryloxy or acylamine.

16. The method according to claim 10 wherein $R_6$ is methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, eicosyl, docosyl, vinyl, allyl, propenyl, octadienyl, octenyl, decenyl, dodecenyl, tetradecenyl, hexadecenyl, octadecenyl, octadecadienyl, nonadecenyl, octadecatrienyl, arachidonyl, —CH$_2$CH(CH$_3$)OCOR$_1$, —CH(CH$_3$)CH$_2$OCOR$_1$, —CH$_2$CH(OCOR$_1$)CH$_2$OCOR$_1$, —CH(CH$_2$OCOR$_1$)$_2$, —CH$_2$CH(OH)CH$_2$OCOR$_1$, —CH$_2$CH(CH$_2$OH)OCOR$_1$, —CH(CH$_2$OH)CH$_2$OCOR$_1$ or —CH(CH$_3$)COOR$_1$.

* * * * *

UNITED STATES PATENT AND TRADEMARK OFFICE
CERTIFICATE OF CORRECTION

PATENT NO. : 5,614,510
DATED : March 25, 1997
INVENTOR(S) : Lars Persson

It is certified that error appears in the above-indentified patent and that said Letters Patent is hereby corrected as shown below:

Column 3, line 24; delete second occurrence of "tridecyl,"

Column 5, line 50: "m" should read --mg--

Column 7, line 44: "biophosphonate" should read --bisphosphonate--

Column 8, line 2: "derivative" should read --derivatives--

Column 8, line 46: "1 hr, 4 hrs," should read --1 hr, 2 hrs, 4 hrs,--

Column 11, line 12, Claim 3: "hepty" should read --heptyl--

Column 11, line 35, Claim 5: "$COOR_6$" should read --$OCOR_6$--

UNITED STATES PATENT AND TRADEMARK OFFICE
CERTIFICATE OF CORRECTION

PATENT NO. : 5,614,510
DATED : March 25, 1997
INVENTOR(S) : Lars Persson

It is certified that error appears in the above-indentified patent and that said Letters Patent is hereby corrected as shown below:

```
        Column 11, line 45, Claim 6:
"inositoltriphosphate"  should read  --inositoltrisphosphate--
        Column 11, line 48, Claim 8:   "1-7in"
should read --1-7 in--
        Column 11, line 50, Claim 9:   "1-7in"
should read --1-7 in--
```

Signed and Sealed this

Fourteenth Day of April, 1998

Attest:

BRUCE LEHMAN

*Attesting Officer*  *Commissioner of Patents and Trademarks*